United States Patent
Nativ et al.

(10) Patent No.: US 12,357,722 B2
(45) Date of Patent: Jul. 15, 2025

(54) SEALANT DRESSING WITH REMOVABLE INTERMEDIATE SEPARATING LAYER

(71) Applicant: Ethicon, Inc., Somerville, NJ (US)

(72) Inventors: Nir Nativ, Somerville, NJ (US); Gerard Llanos, Somerville, NJ (US); Thomas Weindl, Somerville, NJ (US); Sai Veruva, Somerville, NJ (US)

(73) Assignee: Ethicon, Inc., Raritan, NJ (US)

( * ) Notice: Subject to any disclaimer, the term of this patent is extended or adjusted under 35 U.S.C. 154(b) by 147 days.

(21) Appl. No.: 16/934,982

(22) Filed: Jul. 21, 2020

(65) Prior Publication Data

US 2022/0023488 A1    Jan. 27, 2022

(51) Int. Cl.
| | | |
|---|---|---|
| *A61L 15/42* | (2006.01) | |
| *A61L 15/22* | (2006.01) | |
| *A61L 15/28* | (2006.01) | |
| *A61L 15/32* | (2006.01) | |
| *A61L 15/58* | (2006.01) | |

(52) U.S. Cl.
CPC ............ *A61L 15/425* (2013.01); *A61L 15/225* (2013.01); *A61L 15/28* (2013.01); *A61L 15/325* (2013.01); *A61L 15/58* (2013.01); *A61L 2300/608* (2013.01); *A61L 2400/04* (2013.01)

(58) Field of Classification Search
CPC ...... A61L 15/00; A61L 15/225; A61L 15/425; A61L 15/28; A61L 15/325; A61L 15/58; A61L 26/00; A61L 2300/608; A61L 2400/04; A61F 13/00; A61F 13/00008; A61F 13/00021; A61F 13/023; A61F 13/0266; A61F 2013/00259; A61F 2013/00089; A61F 2013/00744; A61F 2013/15934; A61F 2013/53062; A61K 47/6939
USPC .......... 602/41–43, 45, 49, 52, 900; 604/304; 424/443, 445
See application file for complete search history.

(56) References Cited

U.S. PATENT DOCUMENTS

| | | | |
|---|---|---|---|
| 3,364,200 A | | 1/1968 | Ashton et al. |
| 3,871,376 A | * | 3/1975 | Kozak ..................... A61L 15/52 607/114 |

(Continued)

FOREIGN PATENT DOCUMENTS

| | | |
|---|---|---|
| CA | 3053647 A1 | 9/2018 |
| EP | 2279711 A1 | 2/2011 |

(Continued)

OTHER PUBLICATIONS

International Search Report dated Oct. 8, 2021 for International Application No. PCT/IB2021/056501.

(Continued)

*Primary Examiner* — Caitlin A Carreiro
(74) *Attorney, Agent, or Firm* — David R. Crichton; Leo B. Kriksunov

(57) ABSTRACT

The present invention is directed to medical devices having a first porous substrate layer with at least a surface coating thereon of a first co-reactive component and a second substrate layer with at least a surface coating layer of a second co-reactive component that reacts with the first co-reactive component, and a removable barrier layer positioned between the first substrate layer and second substrate layer and in contact with said first substrate layer and said second substrate layer.

25 Claims, 8 Drawing Sheets

(56) References Cited

U.S. PATENT DOCUMENTS

| | | | |
|---|---|---|---|
| 4,626,253 | A | 12/1986 | Broadnax, Jr. |
| 5,002,551 | A | 3/1991 | Linsky et al. |
| 5,007,916 | A | 4/1991 | Linsky et al. |
| 5,180,398 | A | 1/1993 | Boardman et al. |
| 5,484,913 | A | 1/1996 | Stilwell et al. |
| 6,152,943 | A | 11/2000 | Sawhney |
| 6,165,201 | A | 12/2000 | Sawhney et al. |
| 6,179,862 | B1 | 1/2001 | Sawhney |
| 6,443,964 | B1 | 9/2002 | Ory et al. |
| 6,500,777 | B1 | 12/2002 | Wiseman et al. |
| 6,514,534 | B1 | 2/2003 | Sawhney |
| 6,566,406 | B1 | 5/2003 | Pathak |
| 6,605,294 | B2 | 8/2003 | Sawhney |
| 6,673,093 | B1 | 1/2004 | Sawhney |
| 6,703,047 | B2 | 3/2004 | Sawhney et al. |
| 6,818,018 | B1 | 11/2004 | Sawhney |
| 7,009,034 | B2 | 3/2006 | Pathak et al. |
| 7,021,086 | B2 | 4/2006 | Ory et al. |
| 7,335,220 | B2 | 2/2008 | Khosravi et al. |
| 7,347,850 | B2 | 3/2008 | Sawhney |
| 8,470,355 | B2 * | 6/2013 | Skalla .................. A61L 31/146 606/151 |
| 9,272,073 | B2 | 3/2016 | Ladet et al. |
| 9,855,372 | B2 | 1/2018 | Ladet |
| 9,889,230 | B2 | 2/2018 | Bennett et al. |
| 10,525,170 | B2 | 1/2020 | Havenstrite et al. |
| 2003/0035786 | A1 | 2/2003 | Hendriks et al. |
| 2005/0004599 | A1 * | 1/2005 | McNally-Heintzelman ................ A61L 24/0094 606/213 |
| 2005/0080372 | A1 | 4/2005 | Nielsen et al. |
| 2005/0113849 | A1 | 5/2005 | Popadiuk |
| 2008/0071300 | A1 | 3/2008 | Popadiuk et al. |
| 2008/0260802 | A1 | 10/2008 | Sawhney et al. |
| 2010/0152683 | A1 | 6/2010 | Lindgren et al. |
| 2010/0280546 | A1 | 11/2010 | Campbell et al. |
| 2011/0045047 | A1 * | 2/2011 | Bennett .................. A61L 27/34 424/422 |
| 2011/0189287 | A1 | 8/2011 | Abbott et al. |
| 2011/0251574 | A1 | 10/2011 | Hedrich et al. |
| 2014/0249575 | A1 | 9/2014 | Mylonakis et al. |
| 2017/0319193 | A1 * | 11/2017 | Pulapura ............ A61B 17/0401 |
| 2018/0028166 | A1 | 2/2018 | Mylonakis et al. |
| 2022/0062492 | A1 | 3/2022 | Weindl et al. |

FOREIGN PATENT DOCUMENTS

| | | | | |
|---|---|---|---|---|
| GB | 2485637 | A | | 5/2012 |
| WO | 2007/117237 | A1 | | 10/2007 |
| WO | WO-2010002435 | A2 | * | 1/2010 ............ A61L 15/28 |
| WO | 2010059280 | A2 | | 5/2010 |
| WO | 2018/165409 | A1 | | 9/2018 |
| WO | 2022/043796 | A1 | | 3/2022 |

OTHER PUBLICATIONS

International Search Report and Written Opinion, received for PCT Application No. PCT/IB2021/057063, mailed on Oct. 20, 2021, 11 pages.

Xiaowei, He, "Functional Material of Carbohydrate", China Light Industry Press, pp. 328, Jan. 2007.

Zhengnong, Xia, "(Dacihai: Chemical Industry Light Industry Textile Volume", Shanghai Lexicographical Publishing House, p. 222, Aug. 2009.

* cited by examiner

SEALANT DRESSING WITH REMOVABLE INTERMEDIATE SEPARATING LAYER

BACKGROUND

Absorbable hemostatic patches containing two cross-linkable components have been described in the literature including in US Publication No. 2011/0045047 A1. The cross-linkable components for such patches can be a pair of co-reactive compounds or a substrate coated with a co-reactive compound having available units that can form covalent crosslinks with the corresponding co-reactive group on the substrate. The major constraints for such patents is that the co-reactive components can react in an aqueous/moist environment which may reduce the patch potency over time. One practice for overcoming this problem has been to process and package the co-reactive containing patches under low moisture conditions. Another practice has been to create some space or separation between the co-reactive layers by applying coatings on opposite sides of a dressing or by placing a film barrier layer between the co-reactive components.

Applicants have identified an alternative method wherein an inert, removable separator barrier layer is positioned between the co-reactive components to function as a non-permeable and chemically inert physical barrier that prevents interaction. Such separator layer can also serve as a desiccant to remove moisture from the dressing immediate environment. The separating layer can be removed in a way that does not alter the configuration of the patch and in a way that does not require additional procedural steps by the user. In this method, each of the two coated layers can be separated by primary packaging material (no additional barrier in the system) in a way that when the device is removed from the package, the barrier (part of the package) will be removed from the layers and enable their approximation prior to application of the device. Applicants have also identified a method in which the two layers are positioned in the primary package flat away from each other while connected along one of their edges (as an open book, for example) to prevent premature interaction between the layers in the package.

SUMMARY OF THE INVENTION

Figure 1A:
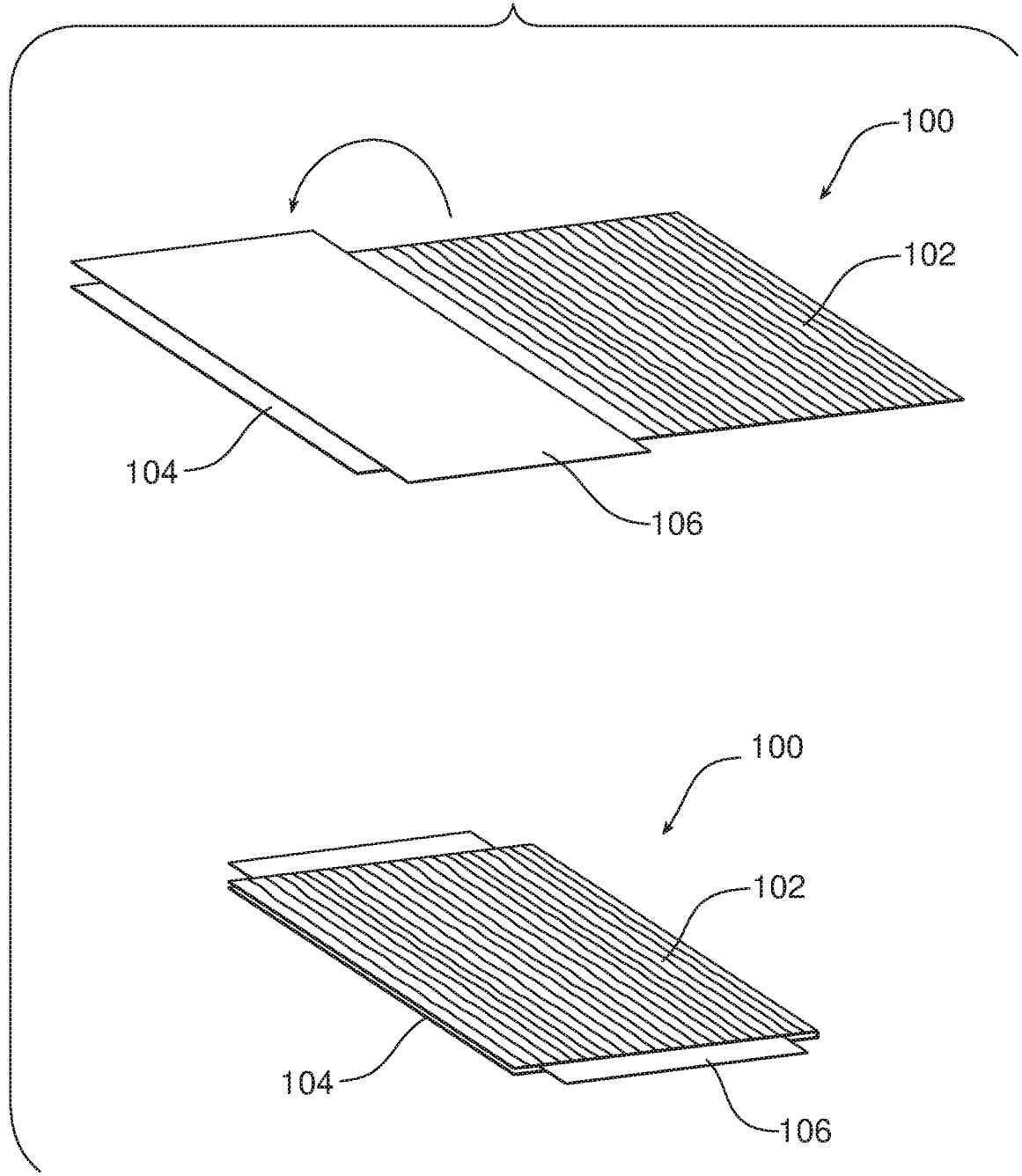
FIGS. 1a and 1b illustrate an embodiment of the present invention in which a single substrate is coated separately on two halves and folded at their border and an intermediately positioned, removable barrier layer or film may be used to physically separate the two co-reactive layers, or optionally stored open with no barrier layer.

In one embodiment, the present invention is directed to medical devices having a first porous substrate layer have at least one major facing surface with at least a surface coating thereon of a first co-reactive component; a second substrate layer having at least one major facing surface with at least a surface coating layer of a second co-reactive component that reacts with the first co-reactive component; and a removable barrier layer positioned between the first substrate layer and second substrate layer and in contact with at least one major facing surface or a surface coating, each, independently of one another, from said first substrate layer and said second substrate layer. The first substrate layer can be a porous, non-woven mesh constructed from one or more synthetic polymers or copolymer, cellulosic materials, and blends thereof. The second substrate layer is a porous, non-woven mesh constructed from one or more synthetic polymers or copolymer, cellulosic materials, and blends thereof. The second substrate layer can be a non-porous film, optionally applied onto a top facing surface of the second substrate layer.

In one embodiment, at least one major surface of the first substrate layer can be coated with a nucleophilic group-containing compound as the first co-reactive component. Alternatively, at least one major surface of the second substrate layer can be coated with an electrophilic group-containing compound as the second co-reactive component. Alternatively, at least one major surface of a substrate layer can be coated PEG-NETS, wherein the PEG-NETS can be coated on a tissue-facing surface. Still further, the PEG-NETS containing substrate can be coated on both sides, while a PEG-amine component can be coated on only one side of an opposing porous substrate layer (sublayer).

In another embodiment, the second co-reactive component can further comprise an activator for the first co-reactive component, wherein the activator can be selected from the group consisting of enzyme, buffering agent, carbodiimides, catalysts and combinations thereof.

In one embodiment, the first substrate layer, the second substrate layer and the barrier layer can be assembled in a sandwich configuration in which the at least three layers are stacked. Further, the first substrate layer and second substrate layer in any embodiment can maintained in common relative positioning with a plurality of connection points or welds.

In one embodiment, the first substrate layer and second substrate layer can be formed by folding a common substrate material along a hinge.

In one embodiment, the first substrate layer and second substrate layer have edge periphery regions and said plurality of connection points or welds are provided on discreet points along at least one edge periphery region on each of the first substrate layer and second substrate layer. At least a plurality of connection points or welds can be provided through said inert film along an axis of the first substrate layer and said second substrate layer. The barrier layer can have one or more slits along at least a length portion thereof corresponding to the plurality of connection points or welds that permits said inert film to be removed from between said first substrate layer and second substrate layer by pulling without having to tear the barrier layer.

In one embodiment, at least one peripheral edge of the barrier layer can extend beyond a peripheral edge of at least one of the first substrate layer and the second substrate layer. Still further, the device can further comprise one or more packaging components, wherein the barrier layer is attached to the packaging and removed as the medical device is separated from the associated one or more packaging components. At least one of the packaging components can be a containment compartment having two spatially separate sections for the first and second substrate layers. The containment compartment can be formed as a single section to retain the first and second substrate layers.

In one embodiment, the present invention is directed to methods to achieve hemostasis on a bleeding site comprising applying the devices described herein onto a bleeding tissue site. In the alternative, a PEG-NETS coated substrate can be applied directly upon the bleeding tissue site.

In one embodiment, the present invention is directed to methods for sealing tissue comprising applying the devices described herein onto an injured tissue site. In an alternative, a PEG-NETS coated substrate can be applied directly upon the injured tissue site.

DETAILED DESCRIPTION

Dressing 100 of the present invention includes a medical device having a substrate construct of at least two fibrous and/or porous sublayers 102 and 104 that contain co-reactive, crosslinkable components. A further outer layer (not shown) that is non-porous (a contiguous film, for example) can be applied over a surface of the medical device that is intended to face away from the tissue surface for multiple purposes, such as providing a sideness feature that enables proper directional placement or as a barrier layer that retains and redirects fluid passing within the medical device.

Each sublayer 102, 104 will have a major facing surface, one or more peripheral edge regions and one or more side depth regions. The number of peripheral edge regions and side depth regions will depend upon the shape of the medical device.

Figure 1B:
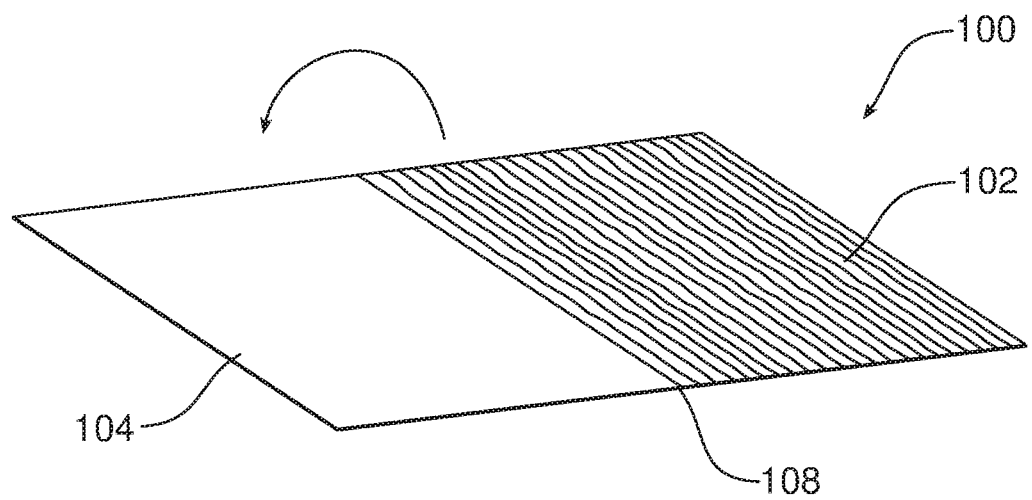
Figure 2:
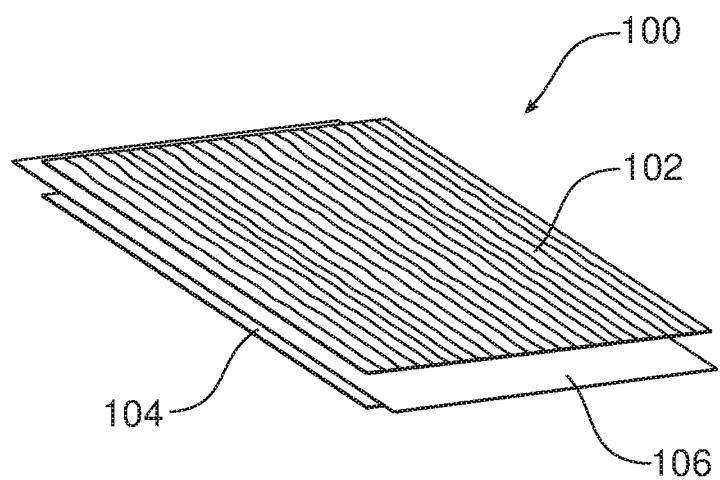
FIG. 2 illustrates an embodiment of the present invention in which two discrete substrate layers are physically separated by an intermediately positioned, removable barrier layer or film.

Further, each sublayer 102, 104 is provided, at least as a surface coating, more preferably as a coating of a reactive and crosslinkable component on the surface that extends into all or some of the depth of the sublayer. These reactive component coatings are physically separated from one another such as by an intermediate placed and removable barrier layer. The medical device or dressing 100 can be composed of a single substrate construct (matrix, for example) material that is coated differently on two subsections, preferably about in halves, to be folded along a border 108 between the two actives, as shown in FIG. 1b, to produce dressing 100 with stacked sublayers 102 and 104 separated by a removable layer 106, as shown in FIG. 1a. In an alternative embodiment, the substrate construct can have at least two discrete, separate co-reactive-containing sublayers 102, 104 with an intermediately positioned, removable barrier layer 106 as shown in FIG. 2.

Figure 3A:
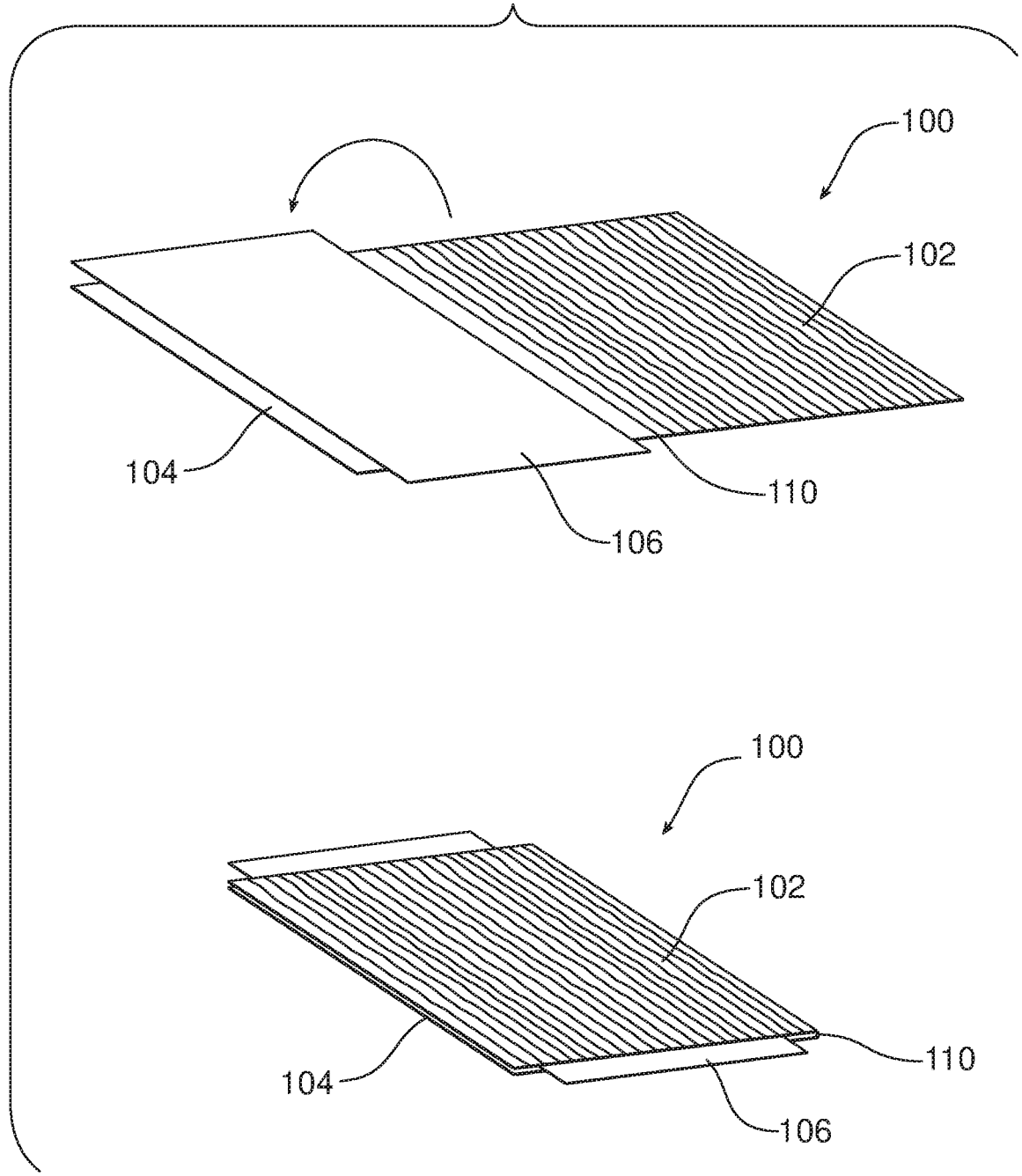
FIGS. 3a and 3b illustrate an embodiment of the present invention in which two discrete substrate layers are coated separately and joined at a hinge and an intermediately positioned, removable barrier layer or film may be used to physically separate the two co-reactive layers, or optionally stored open with no barrier layer.
Figure 3B:
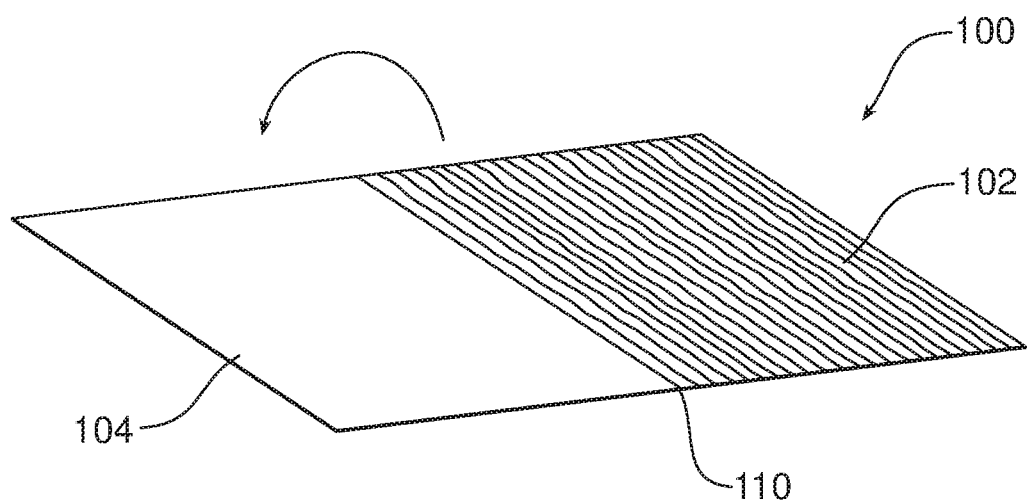
Figure 4:
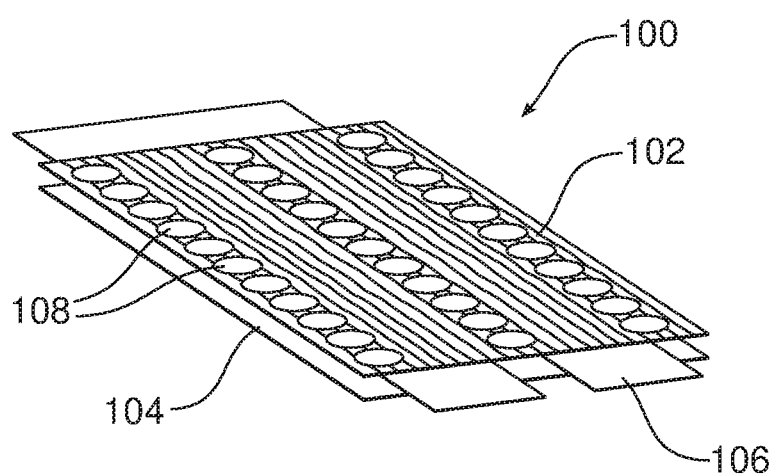
FIG. 4 illustrates an embodiment of the present invention in which two discrete substrate layers are joined at specific "welding" points and an intermediately positioned, removable barrier layer or film is used to physically separate the two layers.
Figure 5:
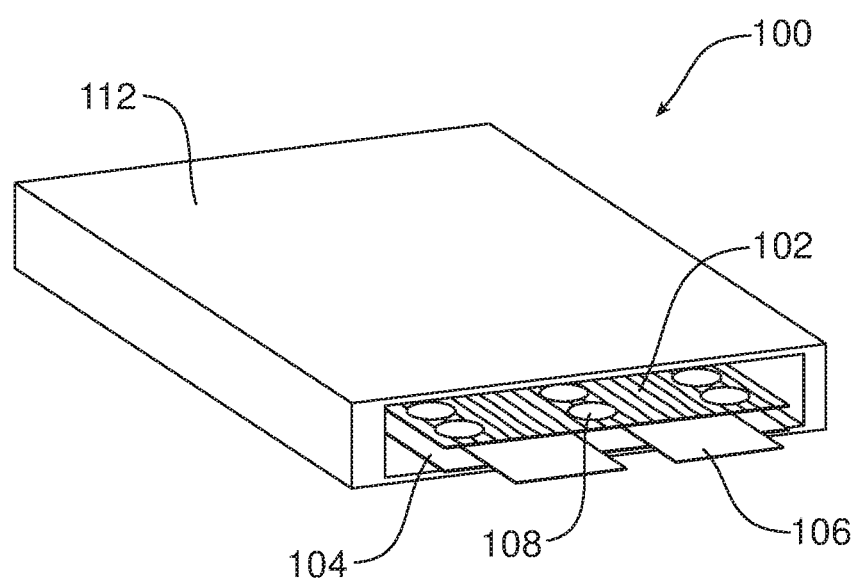
FIG. 5 illustrates an embodiment of the present invention in which two discrete substrate layers are joined at specific "welding" points and an intermediately positioned, removable barrier layer or film is used to physically separate the two layers and the separating layer is affixed to or integrated with the packaging of the device such that removal of the device from said packaging ensures removal of the barrier layer.

Sublayers 102 and 104 can be structurally integrated with one another via ultrasonic welding shown as welding points 108 in FIG. 4, needle punching, heat welding, chemical attachment, suture attachment in order to retain relative positional stability though each layer is otherwise physically distinct and separated. Medical device 100 can be constructed as a bifold construct having two a hinge 110 between coated sublayers 102 and 104 with an intermediately positioned, removable separator barrier layer 106, as shown in FIGS. 3a and 3b. In an alternative embodiment, the substrate construct can have at least two discrete, separate co-reactive-containing sublayers 102 and 104 that are structurally integrated at specific points 108, and with an intermediately positioned, removable barrier layer 106 as shown in FIG. 4, or FIG. 5 where said barrier layer 106 is integrated with secondary packaging 112 of the device.

The co-reactive carrier layers of the substrate construct can be in the form of woven, non-woven or porous sponge materials. Exemplary materials of construction are cellulosic, synthetic polymers, gelatin, collagen and extra cellular matrix. The substrate may be comprised of components selected from gelatin, collagen, oxidized polysaccharides, aliphatic polyester polymers and/or copolymers of one or more monomers selected from the group consisting of D-lactic acid, L-lactic acid, lactide (including L-, D-, meso forms), glycolic acid, glycolide, caprolactone, p-dioxanone and trimethylene carbonate and mixtures or blends thereof. Biodegradable polyurethanes prepared using, but not limited to, diisocyanates such as Ethyl 2,6-diisocyanatohexanoate (ELDI) and Methyl 2,6-diisocyanatohexanoate (MLDI) together with degradable aliphatic polyester diols and with degradable chain extenders such as 2-Hydroxyethyl-2-hydroxypropanoate, 4-((1-(1-Amino-2-phenylethoxy) ethoxy) methylcyclohexyl) methyl-2-amino-3-phenylpropanoate, 1,1-(Hexane-1,6-diyl) bis(3-(2-hydroxyethylurea, Ethane-1, 2-diyl bis(3-(4-hydroxyphenyl) propanoate, Bis(2-hydroxyethyl) phosphate and Bis(2-hydroxyhexyl) phosphate may also be suitable for preparing the substrates.

In one form, the substrate construct may be comprised of layers of oxidized polysaccharides, in particular oxidized cellulose and the neutralized derivatives thereof. For example, the cellulose may be carboxylic-oxidized or aldehyde-oxidized cellulose. In one form, oxidized regenerated polysaccharides including, but without limitation, oxidized regenerated cellulose may be used. Regenerated cellulose possesses a higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents of which are hereby incorporated by reference as if set forth in its entirety. Examples of fabrics that may be utilized include, but are not limited to, Interceed absorbable adhesion barrier, Surgicel® absorbable hemostat; Surgicel® Nu-Knit absorbable hemostat; and Surgicel® Fibrillar absorbable hemostat; each available from Ethicon, Inc., Somerville, N.J. U.S. Pat. No. 5,007,916 discloses the aforementioned Interceed absorbable adhesion barrier and methods for making same, the contents of which are hereby incorporated by reference for all that they disclose.

The substrate may alternatively, or additionally, be comprised of layers of fabric of aliphatic polyester polymers, copolymers, or blends thereof. The aliphatic polyesters are typically synthesized in a ring opening polymerization of monomers including, but not limited to, lactide (including L-, and D-, meso forms), glycolic acid, glycolide, caprolactone, p-dioxanone (1,4-dioxan-2-one), and trimethylene carbonate (1,3-dioxan-2-one). The aliphatic polyesters, in some cases, can be made by polycondensation of, for instance, D-lactic acid, L-lactic acid and/or glycolic acid. In one form, the fabric comprises a copolymer of glycolide and lactide, in an amount ranging from about 70 to 95% by molar basis of glycolide and the remainder lactide.

The substrate construct may also comprise an oxidized regenerated cellulose/polypropylene/polydioxanone (PDS) mesh, commercially available from Ethicon, Inc. under the tradename, Proceed. U.S. Patent Publication Nos. 2005/0113849A1 and 2008/0071300A1 disclose the aforementioned Proceed oxidized regenerated cellulose/polypropylene/PDS mesh substrate and methods for making same, the contents of which are hereby incorporated by reference for all that they disclose. In one form, both exterior surfaces of the oxidized regenerated cellulose/polypropylene/PDS mesh may be substantially coated with the polymeric coating, and in another form only one exterior surface of this substrate may be substantially coated with the polymeric coating. The fabric used to form the substrate may be comprised of aliphatic polyester polymers, copolymers, or blends thereof alone or in combination with oxidized polysaccharide fibers.

In one embodiment, the substrate is made from layers of biomaterials selected from the group consisting of a biomaterial, preferably a protein, a biopolymer or a polysaccharide matrix, especially a collagen, gelatin, fibrin, starch or chitosan matrix. Preferably, the matrix of the present invention is biodegradable, i.e. it is naturally absorbed by the patient's body after some time. In any way, the material (including the matrix) must be biocompatible, i.e. have no harming effect to the patient to whom the material is administered. Such biodegradable materials are specifically suitable in situations where hemostasis is achieved inside the body, i.e. in the course of surgery and the site is closed after surgery.

Accordingly, in one embodiment, the one or more sublayers of the substrate construct is preferably a biomaterial selected from biopolymers such as a protein, or a polysaccharide. Especially preferred is a biomaterial selected from the group consisting of collagen, gelatin, fibrin, a polysaccharide, e.g. hyaluronic acids, chitosan, and a derivative thereof, more preferred gelatin, collagen and chitosan, especially preferred gelatin and collagen. Such gelatin or collagen matrix used for the present invention can be derived from any collagen suitable to form a gel, including a material from liquid, paste, fibrous or powdery collagenous materials that can be processed to a porous or fibrous matrix as well as particles. The preparation of a collagen gel for the production of a sponge or sheet may include acidification until gel formation occurs and subsequent pH neutralization. To improve gel forming capabilities or solubility the collagen may be (partially) hydrolyzed or modified, as long as the property to form a stable sponge or sheet when dried is not diminished. The matrix used for coupling the thrombin receptor activating agent can be a biopolymer, i.e., a naturally occurring polymer or a derivative thereof, or can be a synthetic polymer. Examples of biopolymers useful in a hemostatic material according to the present invention include polypeptides such as collagen, collagen derivatives such as gelatin, elastin, and elastin derivatives.

Collagen-containing embodiments in accordance with the present disclosure include a porous substrate having a first co-reactive and/or crosslinkable component applied to a first portion of the porous substrate and a second co-reactive and/or crosslinkable component applied to a second portion of the porous substrate. It can be that the different components do not crosslink with each other, but that one component, coated on one of the layers, activates the other component, coated on a separate layer, to be potent and lead to hemostasis upon application.

The porous substrate of the dressing has openings or pores over at least a portion of a surface thereof. As described in more detail below, suitable materials for forming the porous substrate include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous substrate. Woven fabrics, knitted fabrics and open cell foam are illustrative examples of structures in which the pores can be in sufficient number and size so as to interconnect across the entire thickness of the porous substrate. In embodiments, the pores do not interconnect across the entire thickness of the porous substrate. Closed cell foam or fused non-woven materials are illustrative examples of structures in which the pores may not interconnect across the entire thickness of the porous substrate. The pores of the foam porous substrate may span across the entire thickness of porous substrate. In yet other embodiments, the pores do not extend across the entire thickness of the porous substrate, but rather are present at a portion of the thickness thereof. In embodiments, the openings or pores are located on a portion of the surface of the porous substrate, with other portions of the porous substrate having a non-porous texture.

Where the porous substrate or a sublayer thereof is fibrous, the porous substrate or sublayer may be formed using any method suitable to forming fibrous structures, including but not limited to knitting, weaving, non-woven techniques, wet-spinning, electro-spinning, extrusion, co-extrusion, and the like. Suitable techniques for making fibrous structures are within the purview of those skilled in the art. In embodiments, the textile has a three dimensional structure, such as the textiles described in U.S. Pat. Nos. 7,021,086 and 6,443,964, the disclosures of which are incorporated herein by this reference in their entirety.

In embodiments, the porous substrate or sublayer thereof is made from fibers of oxidized cellulose. Such materials are known and include oxidized cellulose hemostat materials commercially available under the trade name SURGICEL®. Methods for preparing oxidized cellulose hemostat materials are known to those skilled in the art and are disclosed, for example in U.S. Pat. Nos. 3,364,200; 4,626,253; 5,484,913; and 6,500,777, the disclosures of which are incorporated herein by this reference in their entirety.

Where the porous substrate or sublayer is a foam, the porous substrate or sublayer may be formed using any method suitable to forming a foam or sponge including, but not limited to the lyophilization or freeze-drying of a composition. The foam may be cross-linked or non-cross-linked, and may include covalent or ionic bonds. Suitable techniques for making foams are within the purview of those skilled in the art.

One or more sublayers of the porous substrate can be at least 0.1 cm thick, in certain embodiments from about 0.2 to about 1.5 cm thick. The size of the pores in the sublayers of the porous substrate can be from about 2 micrometers to about 300 micrometers, in certain embodiments from about 50 micrometers to about 150 micrometers. It is envisioned that the pores of the sublayers of the substrate may be arranged in any manner in the substrate. For example, the pores may be configured in a random or uniform manner. In some embodiments, the pores may be formed with the use of copper alginate to create a honey-comb shaped porous substrate. In still other embodiments, the pores may be configured to create a gradient in the porous substrate. The gradient may further enhance the porous substrates ability to absorb the physiologic fluid and direct the migration of the physiological fluid carrying the first co-reactive component towards the second co-reactive component.

In embodiments, the dressing and its substrate construct is a made from non-denatured collagen or collagen which has at least partially lost its helical structure through heating or any other method, consisting mainly of non-hydrolyzed alpha chains, of molecular weight close to 100 kDa. The term "non-denatured collagen" means collagen which has not lost its helical structure. The collagen used for the dressing of present dressing may be native collagen or atelocollagen, notably as obtained through pepsin digestion and/or after moderate heating as defined previously. The collagen may have been previously chemically modified by oxidation, methylation, ethylation, succinylation or any other known process. The collagen may also be cross-linked with any suitable crosslinker, such as genipin, isocyanates, and aldehydes. The origin and type of collagen may be as indicated for the non-dressing described above.

In other embodiments, gelatin or collagen, including any collagen described herein, may be utilized as one of the precursors. As described in greater detail below, amine groups on a collagen precursor, which are nucleophilic, may be free to react with electrophilic groups on a first co-reactive component, thereby forming a substrate of the present disclosure.

In embodiments, the substrate or a porous collagen layer thereof can be obtained by freeze-drying an aqueous acid solution of collagen at a concentration of 2 to 50 grams/liter (g/l) and an initial temperature of 4 to 25 C. The concentration of collagen in the solution can be from about 1 g/l to about 30 g/l, in embodiments about 10 g/l. This solution is advantageously neutralized to a pH of around 6 to 8. The dressing can also be obtained by freeze-drying a fluid foam prepared from a solution of collagen or heated collagen, emulsified in the presence of a volume of air in variable respective quantities (volume of air: water varying from about 1 to about 10).

In one embodiment, the substrate construct has a first co-reactive component applied onto a first sublayer and a second co-reactive component applied thereto. The terms "first co-reactive component" and "second co-reactive component" each means a polymer, functional polymer, macromolecule, small molecule, or crosslinker that can take part in a reaction to form a network of crosslinked molecules, such as, a hydrogel.

In one embodiment, each of the first and second co-reactive components is multifunctional, meaning that it comprises two or more electrophilic or nucleophilic functional groups, such that, for example, a nucleophilic functional group on the first co-reactive component may react with an electrophilic functional group on the second co-reactive component to form a covalent bond. At least one of the first or second co-reactive components includes more than two functional groups, so that, as a result of electrophilic-nucleophilic reactions, the precursors combine to form crosslinked polymeric products. Such reactions are referred to as "crosslinking reactions".

In certain embodiments, each of the first and second co-reactive components includes only one category of functional groups, either only nucleophilic groups or only electrophilic functional groups, so long as both nucleophilic and electrophilic precursors are used in the crosslinking reaction. Thus, for example, if the first co-reactive component has nucleophilic functional groups such as amines, the second co-reactive component may have electrophilic functional groups such as N-hydroxysuccinimide (NHS). On the other hand, if the first co-reactive component has electrophilic functional groups such as sulfosuccinimides, then the second co-reactive component may have nucleophilic functional groups such as amines or thiols. Thus, functional polymers such as proteins, poly(allyl amine), Sulfhydryl (or thiol) terminated PEG., or amine-terminated di- or multifunctional poly(ethylene glycol) ("PEG") can be used.

The first and second co-reactive components may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxymethylcellulose, hyaluronic acid; and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second co-reactive components water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

In embodiments, both the first and second co-reactive components may be large molecules that are capable of cross-linking. For example, in embodiments, one of the precursors may be a multi-functional PEG having a molecular weight of from about 2,000 to about 20,000 Daltons. This multi-functional PEG, in embodiments possessing electrophilic groups, may be reacted with a collagen having a molecular weight of about 100,000 Daltons. In other embodiments, a gelatin having a molecular weight of from about 50,000 to about 100,000 Daltons may be used in place of the collagen.

If it is desired that the biocompatible crosslinked polymer resulting from the reaction of the first and second co-reactive components be biodegradable or absorbable, one or more of the first and second co-reactive components may have biodegradable linkages present between the functional groups. The biodegradable linkage optionally also may serve as the water-soluble core of one or more of the precursors. In the alternative, or in addition, the functional groups of the first and second co-reactive components may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, d-lactide, lactide, caprolactone, dioxanone, and trimethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s as well as degradable polyurethanes. In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional electrophilic polymer such as a multi-arm PEG functionalized with multiple NHS groups may be used as a first co-reactive component, and a multifunctional nucleophilic component such as trilysine may be used as a second co-reactive component. In other embodiments, a multifunctional electrophilic polymer such as a multi-aim PEG functionalized with multiple NHS groups may be used as a first co-reactive component, and a multifunctional nucleophilic polymer such as collagen and/or a collagen derivative may be used as a second co-reactive component. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

Referring to FIG. 1, the first co-reactive component can be applied to a first portion 102 of the porous substrate and a second co-reactive component applied to a second portion 104 of the porous substrate. For example, the precursors may be applied in a dry form, such as particulate matter or in a solid or semi-solid state such as a film, or foam. In embodiments, at least one of the first or second co-reactive components is applied to the porous substrate as a film. The first co-reactive component may be applied to the porous substrate using any suitable method known to those skilled in the art, including, but not limited to spraying, brushing, dipping, pouring, laminating, etc. In embodiments, the first co-reactive component may be applied as a coating on the substrate in any concentration, dimension and configuration capable of forming a hemostatic dressing.

In certain embodiments, the first co-reactive component coating may penetrate the pores of the porous substrate construct. The coating may form a non-porous layer or a porous layer. In certain embodiments, the first co-reactive component may be applied as a film that is laminated onto at least one side of the substrate.

The second co-reactive component likewise may be applied to the porous substrate using any suitable method known to those skilled in the art, including, but not limited to spraying, brushing, dipping, pouring, laminating, etc.

In embodiments, the second co-reactive component may be incorporated into the porous substrate prior to forming the porous substrate. In other embodiments, the second co-reactive component may be positioned in the pores of the porous substrate or onto a surface of the porous substrate following formation of the substrate. In yet other embodiments, the porous substrate may be calendered prior to application of the second co-reactive component thereby allowing the second precursor to penetrate into openings on the substrate which were created by the calendering process. In still other embodiments, the second co-reactive component may be applied to the porous substrate in solution followed by evaporation or lyophilization of the solvent. In certain embodiments, the second co-reactive component may be applied to the porous substrate as a coating on at least one side of the substrate or as a film laminated onto at least one side of the substrate.

It should be understood that, as an alternative to foamed collagen or gelatin, the porous substrate construct or a sublayer thereof may be a fibrous structure. Thus, in embodiments, the porous substrate or sublayer may be a fibrous structure, i.e., a woven or non-woven structure. The first and second co-reactive components can be applied to a fibrous porous substrate construct or part thereof using substantially the same techniques described above with respect to foam porous substrate. Accordingly, as with the foam porous substrates described above, where the porous substrate or sublayer is fibrous, the first and/or second co-reactive components may be applied, for example as particles deposited from a solution, non-porous films formed by drying a film-forming solution, or as a foam applied to at least a portion of the fibrous porous substrate.

The barrier layer is non-porous and inert to the co-reactive components as provided on each sublayer or possess a pore size that inhibits passage of co-reactive components, to prevent interaction between the materials in the different layers. The barrier can be or include a desiccant by appropriate selection of materials that reduce moisture levels within the medical device to improve shelf life. Barrier layer 106 prevents adherence of sublayers 102 and 104. Barrier layer 106 can formed as part or integrated with the primary or secondary packaging for the medical device in some embodiments as exemplified in FIG. 5. Barrier layer 106 is generally a flat film layer but can be textured to provide some additional space and separation between the coated sublayer.

Figure 6A:
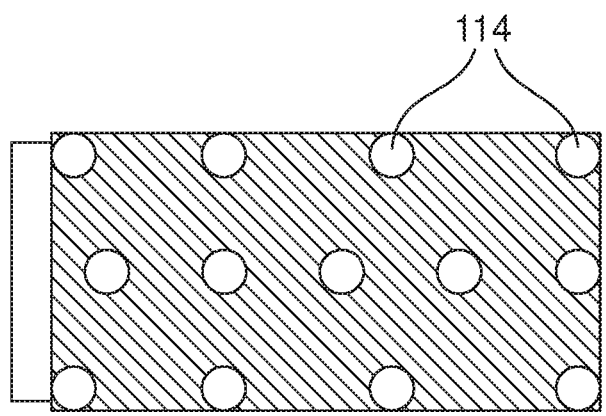
FIGS. 6a and 6b illustrate a barrier layer and an embodiment of the present invention in which the barrier layer possesses holes and cuts along its surface that allows the sublayers to be connected to each other for greater structural integrity.
Figure 6B:
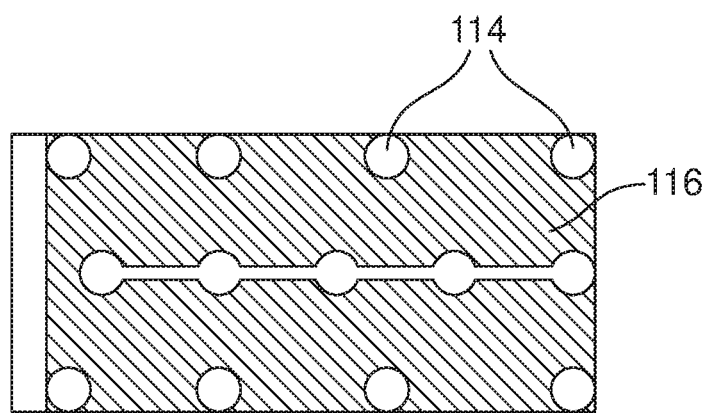

Barrier layer 106 can be positioned between the sublayers 102 and 104 in a way that the barrier layer 106 extends beyond at least one peripheral edge of one or both coated sublayers 102, 104 so the user can grip and remove barrier layer 106 prior to use. In an integrated packaging embodiment of FIG. 5, barrier layer 106 can be attached at least at portion of the package material 112 so that as device 100 is removed from the packaging 112, barrier layer 106 is removed in the same motion from between the coated sublayers 102 and 104. Barrier layer 106 can possess holes 114 and cuts 116 along its surface that allows sublayers 102 and 104 to be connected to each other for greater structural integrity. Such holes 114 and cuts 116, as shown in FIG. 6, at selected points along the peripheral edge regions of the barrier layer 106 are designed in a way that barrier layer 106 can be easily removed from between sublayers 102 and 104 by pulling action. In an alternative embodiment, a slit and optionally openings can be provided at least over a portion of an axis line of the barrier layer to enable interconnections in space other than the peripheral edge regions of the sublayers.

Upon removal of barrier layer 106 and subsequent contact with tissue, physiological fluids will penetrate dressing, migrate and interact with the co-reactive components on different sublayers 102 and 104. It is envisioned that as the fluids are wicked towards first portion 102, a solution will come in contact with the second co-reactive component and be dissolved by and mix with the physiologic fluids. This mixing will activate the first and second precursors and allow them to interact and/or crosslink to form a seal assisting in the sealing and hemostatic function of the dressing 100. In the case that one of the components is an activator for the other, the physiological fluids will enable the activation of the component that can lead to sealing or hemostasis as it meets the tissue or physiological fluids. In certain embodiments, this newly formed hydrogel/physiological fluid dressing could also act as an adhesion barrier.

In one embodiment, one or more sublayers 102 or 104 comprises a nonwoven fabric and a reinforcement fabric. The reinforcement fabric provides a backing to which the nonwoven fabric may be attached, either directly or indirectly. The nonwoven fabric functions as the first absorbable nonwoven fabric of the reinforced absorbable multilayered fabric described herein. The first absorbable nonwoven fabric is comprised of fibers comprising aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, .epsilon.-caprolactone, p-dioxanone (1,4-dioxan-2-one), and trimethylene carbonate (1,3-dioxan-2-one). Preferably, the first absorbable nonwoven fabric comprises a copolymer of glycolide and lactide, in an amount ranging from about 70 to 95% by molar basis of glycolide and the remainder lactide.

In an alternative embodiment, the first absorbable nonwoven fabric comprises fibers comprised of aliphatic polyester polymers, copolymers, or blends thereof, in combination with oxidized polysaccharide fibers. Preferably, the nonwoven fabric is made by processes other than spinning, weaving or knitting. For example, the nonwoven fabric may be prepared from yarn, scrims, netting or filaments that have been made by processes that include spinning, weaving or knitting. The yarn, scrims, netting and/or filaments are crimped to enhance entanglement with each other and attachment to the second absorbable woven or knitted fabric. Such crimped yarn, scrims, netting and/or filaments may then be cut into staple that is long enough to entangle. The staple may be between about 0.1 and 3.0 inches long, preferably between about 0.75 and 2.5 inches, and most preferably between about 1.5 and 2.0 inches. The staple may be carded to create a nonwoven batt, which may be then needlepunched or calendared into the first absorbable nonwoven fabric. Additionally, the staple may be kinked or piled.

The sublayer thickness of the nonwoven fabric may range from about 0.25 to 2 mm. The basis weight of the nonwoven fabric ranges from about 0.01 to 0.2 g/in$^2$; preferably from about 0.03 to 0.1 g/in$^2$; and most preferably from about 0.04 to 0.08 g/in$^2$. The weight percent of first absorbable nonwoven fabric may range from about 10 to 80 percent, based upon the total weight of the reinforced absorbable multilayered fabric.

The second absorbable woven or knitted fabric functions as the reinforcement fabric and comprises oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used to prepare the second absorbable woven or knitted fabric. Regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents each of which is hereby incorporated by reference as if set forth in its entirety.

The reinforcement fabric utilized in the present invention may be woven or knitted, provided that the fabric possesses the physical properties necessary for use in contemplated applications. Such fabrics, for example, are described in U.S. Pat. Nos. 4,626,253, 5,002,551 and 5,007,916, the contents of which are hereby incorporated by reference herein as if set forth in its entirety. In preferred embodiments, the reinforcement fabric is a warp knitted tricot fabric constructed of bright rayon yarn that is subsequently oxidized to include carboxyl or aldehyde moieties in amounts effective to provide the fabrics with biodegradability.

In an alternative embodiment, the second absorbable woven or knitted fabric comprises oxidized polysaccharide fibers in combination with fibers comprised of aliphatic polyester polymers, copolymers, or blends thereof.

The second absorbable woven or knitted fabric preferably comprises oxidized regenerated cellulose and may have a basis weight ranging from about 0.001 to 0.2 g/in$^2$, preferably in the range of about 0.01 to 0.1 g/in$^2$, and most preferably in the range of about 0.04 to 0.07 g/in$^2$.

The first absorbable nonwoven fabric is attached to the second absorbable woven or knitted fabric, either directly or indirectly. For example, the nonwoven fabric may be incorporated into the second absorbable woven or knitted fabric via needlepunching, calendaring, embossing or hydroentanglement, or chemical or thermal bonding. The staple of the first absorbable nonwoven fabric may be entangled with each other and imbedded in the second absorbable woven or knitted fabric. More particularly, for methods other than chemical or thermal bonding, the first absorbable nonwoven fabric may be attached to the second absorbable woven or knitted fabric such that at least about 1% of the staple of the first absorbable nonwoven fabric are exposed on the other side of the second absorbable woven or knitted fabric, preferably about 10-20% and preferably no greater than about 50%. This ensures that the first absorbable nonwoven fabric and the second absorbable woven or knitted fabric remain joined and do not delaminate under normal handling conditions. The reinforced absorbable multilayered fabric is uniform such that substantially none of the second absorbable woven or knitted fabric is visibly devoid of coverage by the first absorbable nonwoven fabric.

In one embodiment, matrix A, which is a combination of a reinforcement and absorbable layers, is sprayed with a reactive PEG, preferably a PEG-amine (NH2), meaning a multi-primary amine functionalized polyethylene glycol derivative and matrix B, which is a non-woven matrix of synthetic polymer, is sprayed with a co-reactive PEG, preferably PEG-NHS, meaning a multi-N-hydroxylsuccinimide (NHS) functionalized polyethylene glycol. These two sublayers are connected to each other at several points along the surface area by means of ultrasonic welding, needle punching, heat welding, chemical attachment, suture attachment, etc. A barrier film is positioned between the two matrixes. The barrier layer is flexible and removed before use, either manually and/or by connection to the outer packaging as the dressing is pulled from the package. The barrier layer can be made of, for example, polyethylene terephthalate (PET) or polystyrene or Tyvek.

During use, the dressing is oriented with the portion to which the first co-reactive component is applied is closer to the tissue and the portion having the second co-reactive component applied thereto is adjacent thereto but further from the tissue. In embodiments, the first and second portions may be distinguishable from one another by the addition of contrast dyes, surface texturing, coloring or other visual cues. Upon contact with tissue, such as, for example, injured tissue, the dressing will soak up physiological fluid and the first hydrogel co-reactive component will be dissolved by the fluid. As the fluid wicks into and migrates across the dressing, it will carry the dissolved first co-reactive component along through the dressing. Eventually, the fluid will migrate through the dressing sufficiently to reach the second portion to which the second co-reactive component is applied, thereby dissolving the second co-reactive component. The first and second co-reactive components will then react to form a biocompatible cross linked material, thereby assisting tissue ingrowth and remodeling as the scaffold degrades. In some embodiments, the biocompatible cross linked material produced by reaction of the first and second co-reactive components also provide the dressing with anti-adhesive properties.

The following example is provided for illustrative purposes only and is not intended to limit the scope of the present disclosure.

EXAMPLE

A 2-inch by 4-inch matrix (Matrix A) was coated with 11.59 mg/cm2 of PEG-NH2 5K (20 grams in 100 ml of acetone) using an ultrasonic spraying machine. Then, two 2-inch by 4-inch PG910 batts (Matrix B) formed from a copolymer of 90% glycolide and 10% L-lactide at two different densities of fiber (8.5 grams/batt and 15.0 gram/batt) were coated with 13.91 mg/cm$^2$ of PEG-NHS 10K (20 grams in 100 ml of acetone) using an ultrasonic spraying machine. The two coated matrices were allowed to dry at room temperature in a nitrogen box overnight, where they were not in physical contact with each other.

The two matrices (A and B) were cut to a 3 cm by 3 cm squares and positioned on top of each other. Then, this overlay was placed over a 10 mm circular biopsy defect in an ex-vivo spleen bleeding model (perfused with heparinized Cow blood) for 2 min with tamponade. The level of bleeding before and after application was evaluated qualitatively (visual observation of bleeding) as well as quantitatively (measuring the amount of blood perfused out of defect in grams per min).

For the matrix in the overlay construct where Matrix B is 8.5 g/batt density. No blood flow observed from the defect post application and the measured blood flow dropped from 27.74 g of blood/min to 0 g of blood.

For the matrix in the overlay construct where Matrix B is 15 g/batt density. No blood flow observed from the defect post application and the measured blood flow dropped from 11.59 g of blood/min to 0 g of blood. It was shown that both batt coated with PEG-NHS (Matrix B) of density 8.5 g/batt and 15 g/batt were efficient in eliminating the bleeding from the defects. In addition, although the two matrices were not mechanically or chemically attached, no delamination of the layers was observed as it seems that the blood and probably activation of the two co-reactive PEGs by the blood joined the layers together at the defect site. Separating the two co-reactive PEGs, however, improved the product stability relative to a patch that is co-coated with the two co-co-reactive PEGs.

We claim:

1. A medical device comprising:
   a. a first porous substrate layer having at least one major facing surface with at least a surface coating thereon of a first co-reactive component in a dry form;
   b. a second substrate layer having at least one major facing surface with at least a surface coating layer of a second co-reactive component in a dry form that reacts with the first co-reactive component; and
   c. a removable inert barrier film layer positioned between the first porous substrate layer and second substrate layer and in contact with at least one major facing surface or a surface coating, each, independently of one another, from said first porous substrate layer and said second substrate layer,
   wherein said inert barrier film layer is removable from between the first porous substrate layer and the second substrate layer by pulling, and wherein at least one peripheral edge of the barrier layer extends beyond a peripheral edge of at least one of the first porous substrate layer and the second substrate layer.

2. A medical device according to claim 1 wherein the first porous substrate layer is a porous, non-woven mesh constructed from one or more synthetic polymers or copolymer, cellulosic materials, and blends thereof.

3. A medical device according to claim 2 wherein the second substrate layer is a porous, non-woven mesh constructed from one or more synthetic polymers or copolymer, cellulosic materials, and blends thereof.

4. A medical device according to claim 3 wherein at least one major surface of the first porous substrate layer is coated with a nucleophilic group-containing compound as the first co-reactive component.

5. A medical device according to claim 4 wherein the first porous substrate layer and second substrate layer are maintained in common relative positioning with a plurality of connection points or welds.

6. A medical device according to claim 5, wherein first porous substrate layer and second substrate layer have edge periphery regions and said plurality of connection points or welds are provided on discreet points along at least one edge periphery region on each of the first porous substrate layer and second substrate layer.

7. A medical device according to claim 6, wherein at least a plurality of connection points or welds are provided through said inert barrier film layer along an axis of the first porous substrate layer and said second substrate layer.

8. A medical device according to claim 5, wherein the barrier layer has a slit along and through at least a length portion thereof corresponding to the plurality of connection points or welds that permits said inert barrier film layer to be removed from between said first porous substrate layer and second substrate layer by pulling without having to tear the barrier layer.

9. A medical device according to claim 3, wherein a non-porous film is applied onto a top facing surface of the second substrate layer.

10. A medical device according to claim 3 wherein at least one major surface of the second substrate layer is coated with an electrophilic group-containing compound as the second co-reactive component.

11. A medical device according to claim 3 wherein the first porous substrate layer, the second substrate layer and the barrier layer are assembled in a sandwich configuration in which the layers are stacked.

12. A medical device according to claim 1 further comprising one or more packaging components, wherein the barrier layer is attached to the one or more packaging components and removed as the medical device is separated from the one or more packaging components.

13. A medical device according to claim 12, wherein at least one of the one or more packaging components is a containment compartment that has two spatially separate sections for the first and second substrate layers.

14. A medical device according to claim 13, wherein the containment compartment is a single section to retain the first and second substrate layers.

15. A medical device according to claim 1, wherein at least one major surface of a substrate layer is coated with polyethylene glycol-N-hydroxysuccinimide.

16. A medical device according to claim 15, wherein the polyethylene glycol-N-hydroxysuccinimide coated substrate is a tissue-facing surface.

17. A medical device according to claim 15, wherein the substrate layer is coated on both sides and a polyethylene glycol-N-hydroxysuccinimide is coated on only one side of an opposing porous substrate.

18. A medical device according to claim 1, wherein the second co-reactive component further comprises an activator for the first co-reactive component.

19. A medical device according to claim 18, wherein the activator is selected from the group consisting of enzyme, buffering agent, carbodiimides, catalysts and combinations thereof.

20. A medical device according to claim 1, wherein the second substrate layer is a non-porous film.

21. A medical device according to claim 1, wherein the first porous substrate layer and second substrate layer are formed by folding a common substrate material along a hinge.

22. A method to achieve hemostasis with the medical device of claim 1 on a bleeding site comprising removing said inert barrier film layer from between said first porous substrate layer and second porous substrate layer by pulling and applying the medical device onto a bleeding tissue site.

23. A method according to claim 22, wherein a polyethylene glycol-N-hydroxysuccinimide coated substrate is applied directly upon the bleeding tissue site.

24. A method for sealing tissue with the medical device of claim 1 comprising removing said inert barrier film layer from between said first porous substrate layer and second substrate layer by pulling and applying the medical device onto an injured tissue site.

25. A method according to claim 24, wherein a polyethylene glycol-N-hydroxysuccinimide substrate is applied directly upon the injured tissue site.

* * * * *